United States Patent [19]

Kuraoka et al.

[11] Patent Number: 4,494,385
[45] Date of Patent: Jan. 22, 1985

[54] METHOD OF PRESERVING ORGAN AND APPARATUS FOR PRESERVING THE SAME

[75] Inventors: Yasuo Kuraoka; Nobuo Sakao, both of Sapporo, Japan

[73] Assignee: Hoxan Corporation, Sapporo, Japan

[21] Appl. No.: 615,212

[22] Filed: May 20, 1984

Related U.S. Application Data

[62] Division of Ser. No. 499,220, May 31, 1983, Pat. No. 4,462,215.

[30] Foreign Application Priority Data

Jun. 4, 1982 [JP] Japan .................................. 57-95896
Mar. 31, 1983 [JP] Japan .................................. 58-56593

[51] Int. Cl.³ .............................................. B01F 3/04
[52] U.S. Cl. .................................. 62/306; 62/514 R; 165/14; 435/1
[58] Field of Search .................. 62/78, 306, 514 R; 435/1; 165/2, 14

[56] References Cited

U.S. PATENT DOCUMENTS

| | | | |
|---|---|---|---|
| 3,406,531 | 10/1968 | Swenson et al. | 62/78 |
| 3,545,221 | 12/1970 | Swenson et al. | 62/78 |
| 3,545,225 | 12/1970 | Swenson et al. | 62/78 |
| 3,607,646 | 9/1971 | Roissart | 435/1 |
| 3,881,990 | 5/1975 | Burton et al. | 435/1 |
| 3,892,628 | 7/1975 | Thorne et al. | 435/1 |
| 3,914,954 | 10/1975 | Doerig | 62/306 |
| 4,008,754 | 2/1977 | Kraushaar et al. | 62/78 |
| 4,186,565 | 2/1980 | Toledo-Pereyra | 62/306 |
| 4,242,883 | 1/1981 | Toledo-Pereyra | 62/78 |

Primary Examiner—Ronald C. Capossela
Attorney, Agent, or Firm—George B. Oujevolk

[57] ABSTRACT

A method of preserving an organ which comprises a first perfusing step of injecting blood uniform i.e., perfusing choline from an artery or portal vein of the excised organ while gradually lowering its temperature and exhausting it from the vein, continuing until the liquid is lowered to the first proximity of a low temperature before its solidifying temperature, second perfusing step of perfusing refrigerating defect-preventing dimethyl sulfoxide or glycerin agent instead of the blood perfusing liquid while gradually lowering the temperature from the first proximity of a low temperature continuing until the agent becomes the second proximity lowering temperature before its solidifying temperature, third perfusing step of perfusing the final perfusing liquid of low solidifying temperature lower than alcohol or ether instead of the agent while gradually lowering the temperature of the liquid from the second proximity of a low temperature and continuing until the liquid reaches the third proximity of a low temperature before its solidfying temperature, or until the liquid is frozen.

4 Claims, 2 Drawing Figures

METHOD OF PRESERVING ORGAN AND APPARATUS FOR PRESERVING THE SAME

This application is a divisional application of U.S. patent application Ser. No. 06/499,220 filed May 31, 1983 now U.S. Pat. No. 4,462,215.

BACKGROUND OF THE INVENTION

This invention relates to a method of preserving an organ of various type excised from a human body for a long period or term to preserve the organ and to transplant the organ at an adequate time to an apparatus for preserving the organ to be used to perform the method.

The preservation of an excised organ to the time of transplanting the organ has heretofore been carried out. The preserving apparatus is known which injecting choline at approx. 4° C. having properties similar to blood from an artery or portal vein of an organ and exhausting the blood from a vein. This is the so-called perfusion method. The organ which is thus treated by this perfusion method is preserved under the temperature conditions of approx. 4° C., and is used after blood is applied to the preserved organ in case of the transplantation.

According to this preserving method, the organ can be preserved only for approximately 12 hours. Accordingly, the timing adjustment between the supply and the demand of the organ becomes difficult, causing large problem to save human life.

The practice is to freeze the organ at a low temperature acting as the preserving temperature condition so as to prolong the preservation time, but when the organ is frozen according to the conventional method, a cell necrocytosis occurs, causing the organ itself to occur a meronecrosis.

SUMMARY OF THE INVENTION

Accordingly, a primary object of this invention is to provide a method of preserving an organ which can freeze the organ without there occurring a cell necrocytosis and can semipermanently preserve the cell and also which can thaw the frozen organ in case of transplanting the organ.

Another object of this invention is to provide an apparatus for preserving and thawing the frozen organ.

The foregoing and other relates objects and features of the invention will be apparent from a reading of the following description of the disclosure taken together with the accompanying drawings and the novelty thereof pointed out in the appended claims.

DESCRIPTION OF THE PREFERRED EMBODIMENTS

An apparatus for preserving an organ according to the present invention will be described with respect to the embodiment disclosed in the accompanying drawings.

Figure 1:
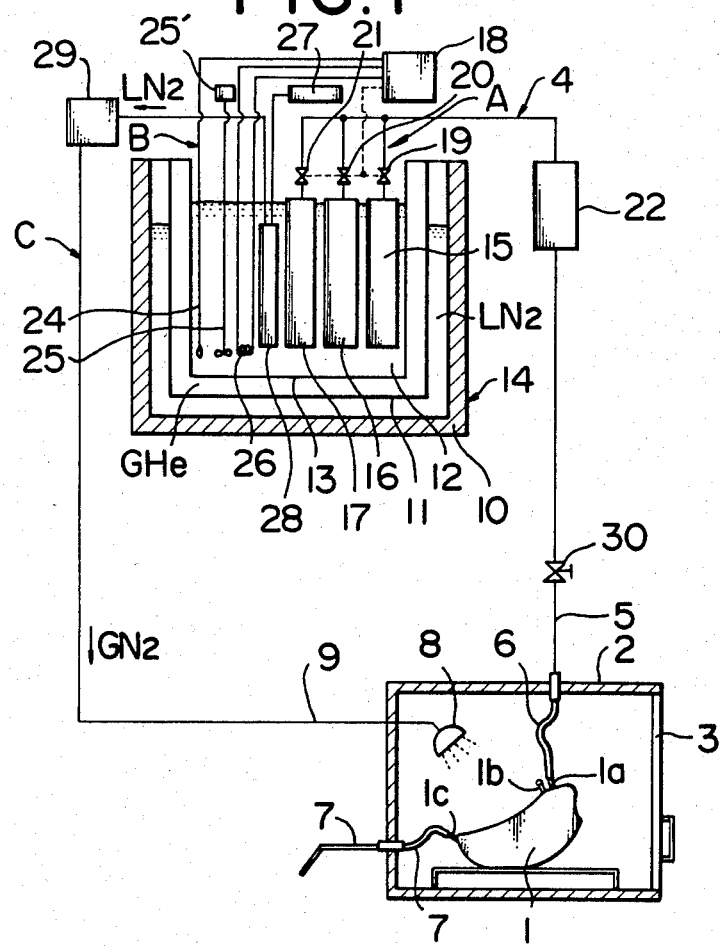
FIG. 1 is a partial longitudinal sectional view for explanatory purpose of one preferred embodiment of an apparatus for preserving an organ to carrying out the method of preserving the organ according to the present invention and FIG. 2 is a schematic view for explanatory purpose of the essential part of another preferred embodiment of the apparatus according to the present invention.

In FIG. 1, a heat insulating container 2 which can contain an organ 1 has an openable door 3. The container 2 and a perfusion freezing and thawing unit 4 are connected to a fluid supply pipe 5 of the unit 4. An inflow pipe 6 which is passed through the container 2 is connected to one end of the pipe 5. This pipe 6 is connected to the artery 1a or a portal vein 1b of the organ 1. Further, an exhaust pipe 7 which is passed through the container 2 is connected to a vein 1c. Then, a gas supply pipe 9 of the unit 4 is connected to a gas supply nozzle 8 which is provided in the container 2. The unit 4 shown in FIG. 1 stores liquefied nitrogen $LN_2$ between outer and middle tanks 10 and 11 which are thermally insulated, and a cooling tank 14 sealed with helium gas GHe between the tank 11 and an inner tank 13 which contains refrigerant 12 such as Freon. A liquid supplying mechanism A is provided in the tank 14.

In the mechanism A shown in FIG. 1, first, second and third containers, 15, 16, 17 which respectively contain an agent, i.e., choline or dimethyl sulfoxide (DMSO), glycerin and alcohol are dipped in the refrigerant 12. First, second and third control valves 19, 20 and 21 respectively provided at outflow pipes of the containers 15, 16 and 17 are suitably opened or closed under the control of a controller 18, and the choline, DMSO and alcohol are selectively supplied to the artery 1a or portal vein 1b of the organ 1 by the operation of a pump 22 provided at the pipe 5.

Figure 2:
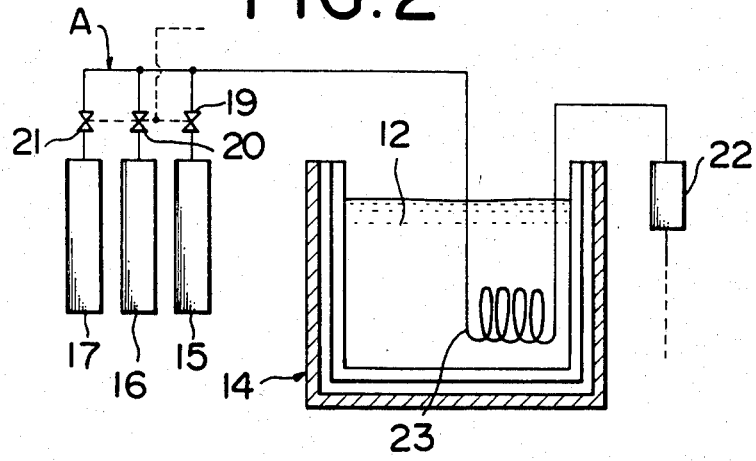

On the other hand, in a liquid supplying mechanism A which is schematically shown in FIG. 2, first, second and third containers 15, 16 and 17 are provided externally of the cooling tank 14, and a heat exchanger 23 formed between the first, second and third control valves 19, 20 and 21 and the pump 22 is dipped in the refrigerant 12 of the cooling tank 14.

In the tank 14 is provided a refrigerant temperature controlling mechanism B which can control the temperature of the refrigerant 12. In the embodiment exemplified in FIG. 1, a temperature sensor 24, an agitator 25 and an electric heater 26 are dipped in the refrigerant 12 in the mechanism B. The sensor 24 and the heater 26 are connected to the controller 18. Reference numeral 25' designates a motor for driving the agitator 25.

Further, in the tank 14 is provided an organ temperature controlling mechanism C. The $LN_2$ is supplied from an organ refrigerant bomb 27 which contains liquid nitrogen to a gas supplying container 28 which is disposed in the refrigerant 12, and the $LN_2$ which is supplied to the nozzle 8 through the pipe 9 as nitrogen gas $GN_2$ controlled to a predetermined temperature by a heat exchanger 29. Reference numeral 30 designates a control valve provided in the pipe 5.

In order to perform the method of preserving an organ according to the present invention with the apparatus thus constructed as described above, the first valve 19 is first opened by the controller 18, and blood uniformly perfused liquid such as choline is supplied from the container 15 by the operation of the pump 22. Thus, the liquid is flowed from the artery 1a or portal vein 1b of the organ 1 into the organ 1, and is exhausted externally from the vein 1c. In this case, the liquid is injected while gradually lowering its temperature by controlling the temperature of the refrigerant 12 under the control of the mechanism B by the controller 18.

More particularly, since the excised organ 1 is initially substantially at 37° C. of human body temperature, the liquid temperature is gradually lowered from the body temperature. Then, the blood of the organ 1 is exhausted by the injection of the liquid into the organ 1 and is thus substituted by the liquid. Such a perfusing step is continued until the liquid reaches the proximity of the first low temperature before reaching the solidifying temperature (hereinafter called "proximity low-temperature" or "proximity temperature").

The above temperature lowering step is controlled by controlling the refrigerant 12 cooled through the GHe in the tank 11 from the $LN_2$ in the tank 10 by the mechanism B. Since the solidifying temperature of the choline is approximately 0° C., the first perfusing step may control the lowering temperature so that the first proximity lowering temperature becomes approximately 1° to 2° C. In order to lower, for example, the blood uniform perfusing liquid from the body temperature of 37° C. to 2° C., the temperature lowering speed is 3.5° C./min, and the perfusing time can be set to approximately 10 minutes.

The $GN_2$ controlled as to its temperature is injected from the nozzle 8 by operating the heat exchanger 29, thereby rapidly equalizing the atmospheric temperature in the container 2 to the temperature of the blood uniformly perfusing liquid the temperature of which is to be lowered so as to eliminate the temperature gradient between the inner and the outer temperatures of the organ 1. This is also continued in the following steps.

Then, the method proceeds to the second perfusing step of supplying and perfusing a freezing defect preventing agent such as dimethyl sulfoxide or glycerin in the container 16 to the organ 1 instead of the blood uniformly perfusing liquid by controlling to close the valve 19 and to open the valve 20 instead of the blood uniformly perfusing liquid.

In this step, the said agent reaches the first proximity of a low (or proximity low) temperature (2° C.). The agent is gradually lowered by controlling it with the mechanism B, and this step is continued until the agent reaches the second proximity low temperature before the solidifying temperature.

Since the solidifying temperature of the DMSO is approximately −5° C., the second proximity lowering temperature is preferably approximately −4° C. In fact, it takes approx. 20 minutes of perfusing period of time at 0.3° C./min to lower the temperature from 2° C. of the first proximity perfusing temperature to −4° C., the moisture content can be sufficiently absorbed by the agent due to the osmotic pressure difference between the agent and the moisture content in the cells of the organ 1 with the perfusion of the agent.

When the second perfusing step is thus completed, the operation is then transferred to the third perfusing step. To transfer to the third step, the valve 20 is closed, the valve 21 is opened to substitute the agent for the final perfusing liquid having a solidifying temperature lower than the above refrigerating defect preventing agent such as alcohol and to supply and perfuse the final perfusing liquid. In this step, the liquid is gradually lowered from the second proximity low temperature (−4° C.), is continued until the final perfusing liquid becomes the third proximity temperature before its solidifying temperature or until the perfusing liquid is frozen to stop perfusing. In case of the alcohol, since the solidifying temperature is approximately −80° C., the third proximity lowering temperature may, for example, be set to −60° C. or −80° C.

In fact, in this third step, it takes approximately 30 minutes of perfusing period of time at the lowering speed of 0.1° C./mins. to lower the alcohol from −4° C. to −37° C., and it further takes approximately 5 minutes of perfusing period of time at the lowering temperature of 5° C./min. under the lowering condition from −7° C. to −60° C.

The frozen organ obtained through the first to third steps as described above is then preserved in the frozen state. In case of the above embodiment, the frozen organ may be preserved in a refrigerator which is maintained at App. −80° C. or may be preserved in liquefied gas such as liquefied nitrogen.

The frozen organ thus preserved is then thawed for transplanting. The thawing means can be performed substantially in reverse to the steps of freezing the organ.

More particularly, the frozen organ is removed from the preserved position, and is set to the state shown in FIG. 1. In this case, the atmospheric temperature in the container 2 is first gradually lowered thereby raising the temperature of the final perfusing liquid such as alcohol existing in a blood vessel of the organ higher than the solidifying temperature to thaw the liquid and then opening the valve 21, thereby perfusing the alcohol by the pump 22.

In the first thawing and perfusing step, the liquid temperature is gradually raised by the mechanism B and is continued until the liquid temperature reaches the second proximity low temperature (−4° C.).

Then, the method is transferred to the second thawing and perfusing step of perfusing the refrigerating defect preventing agent instead of the final perfusing liquid. In this step, the liquid temperature is gradually raised from the proximity of the second low, i.e., the second proximity low temperature (−4° C.), and is continued until the temperature of the agent reaches the proximity of the first low i.e., the first proximity low temperature(1° to 2° C.).

Further, the temperature of the blood uniformly perfusing liquid such as the choline is gradually raised from the first proximity low temperature instead of the agent and is perfused. The third step is continued until the liquid reaches the approximate body temperature. Thus, after the organ passed through all the thawing and perfusing steps it can be used for an organ transplant by applying the predetermined blood to the organ.

According to the first method of the present invention described, the choline is not merely perfused in the organ instead of the blood as the conventional method and the organ is preserved at App. 4° C., but the temperature of the blood perfusing liquid such as choline is gradually lowered in the first perfusing step until the liquid is perfused to the proximity of the first low temperature before its solidifying temperature. Accordingly, the organ is not affected by the action of the abrupt temperature change, but the nutriments equivalent to the blood are supplied to the organ when the metabolism of the cells of the organ is most active at 1° to 2° C.

In the second thawing step, the temperature of the refrigerating defect-preventing agent is further lowered again to the second proximity of the low temperature before the solidifying temperature of the agent. Accordingly, the moisture content in the cells is absorbed due to the osmotic pressure difference from the moisture content in the cells or the organ and the agent in this step as hereinbefore described. Consequently, when the organ is frozen by the drop in temperature in the next step, no moisture is contained, and the organ can be frozen without causing cell necrocytosis.

In the final third thawing step, the thawing is performed while lowering the temperature from −4° C. to −80° C. with the final perfusing liquid of low solidifying temperature lower than the agent as the perfusing liquid. Accordingly, the temperature of the organ can be lowered to a considerably low state without the defect of the abrupt temperature drop in the respective steps.

Therefore, according to the first embodiment of the present invention as described the organ can be semi-permanently preserved without cell meronecrosis by preserving the frozen organ in the frozen state.

In the second embodiment of the present invention, the frozen organ preserved according to the first embodiment of the present invention provides a means to preserve the organ to the state capable of transplanting the organ. In this embodiment, the steps of the first embodiment is performed in reverse. Thus, the temperature of the frozen and preserved organ described is gradually raised at its temperature to thaw the final thawing liquid in the blood vessel in the organ, the temperature of the liquid is then gradually raised the first thawing and perfusing step for perfusing the liquid from the artery or portal vein to the vein until reaching the second proximity low temperature, the refrigerant defect preventing agent is gradually raised from the above second proximity lowering temperature instead of the final perfusing liquid, and is continued until reaching the first proximity low temperature, and further the temperature of the blood perfusing liquid is gradually raised from the first proximity lowering temperature instead of the agent, and is continued until becoming the body temperature in the third thawing and perfusing step of perfusing the liquid, and the predetermined blood is applied to the organ. Therefore, the frozen organ be readily thawed without any damage.

Further, in the third embodiment of the present invention, the apparatus for preserving the frozen organ, which comprises the perfusing and thawing unit 4, and the heat insulating container 2 capable of containing the organ 1, the unit 4 having a refrigerant tank 14 containing the refrigerant 12 such as Freon and thermally insulated, the refrigerant temperature controlling mechanism B capable of controlling the temperature of the refrigerant 12 by the controlle 12, the gas supplying container 28 supplied with the refrigerant from the organ refrigerant bomb 27 dipped in the refrigerant 12 for the tank 14, the container 28 having the organ temperature controlling mechanism C connected through the heat exchanger 21 to the gas supply pipe, and the liquid supplying mechanism A for selectively flowing out the liquid to be flowed out from the first container 15 for blood uniformly perfusing liquid such as choline, the second container 16 for the refrigerating defect-preventing agent such as dimethyle sulfoxide or glycerin, the third container 17 for low solidifying point final perfusing liquid such as alcohol under the control of the controller 18 to the liquid supply pipe 5, the mechanism C being connected via the pipe 9 to the nozzle 8 in the container 2, and the mechanism A being connected to the artery 1a or portal vein 1b in the organ 1 in the container 2 at the pipe 5 and the vein 1c of the organ 1 being prolonged externally of the container 2 via the exhaust pipe 7 capable of being connected to the vein 1c of the organ 1. Therefore, the temperature of the refrigerant 12 can be freely controlled by the mechanism B, the blood uniformly perfusing liquid, the refrigerating defect-preventing agent and the low solidifying point final perfusing liquid can be suitably fed at the controlled temperature via the mechanism A to the organ 1, and yet the temperature of the container 2 can also be controlled by the mechanism C. Consequently, the perfusion of the organ 1 can be performed without undesired temperature gradient, and the method of preserving and thawing the organ can be performed without defect as described in detail.

What is claimed is:

1. An apparatus for preserving a frozen organ comprising:

a perfusing and thawing unit, and a heat insulating container capable of containing said organ, said unit having a refrigerant tank containing the refrigerant such as Freon and thermally insulated, a refrigerant temperature controlling mechanism capable of controlling the temperature of the refrigerant by a controller, a gas supplying container supplied with the refrigerant from an organ refrigerant bomb dipped in the refrigerant for said tank, an organ temperature controlling mechanism connected through a heat exchanger to a gas supply pipe, and a liquid supplying mechanism for selectively flowing out the liquid to be flowed out from a first container for blood uniformly perfusing liquid such as choline, a second container for the refrigerating defect preventing agent such as dimethyle sulfoxide or glycerin, a third container for low solidifying point final perfusing liquid such as alcohol under the control of the controller to a liquid supply pipe, said organ temperature controlling mechanism being connected via a pipe (9) to a nozzle in the container (2), and said liquid supplying mechanism being connected to an artery or portal vein in the organ in the container (2) at the pipe and the vein of the organ being prolonged externally of the container via the exhaust pipe capable of being connected to the vein 1c of the organ.

2. The apparatus as claimed in claim 1, wherein said refrigerant temperature controlling mechanism comprises a temperature sensor connected to said controller, an electric heater, and an agitator.

3. The apparatus as claimed in claim 1, wherein the first, second and third containers of said liquid supplying mechanism are dipped in the refrigerant in said cooling tank, and the opening or closing of said first, second and third control valves provided at said respective container are controlled by said controller.

4. The apparatus as claimed in claim 1, wherein the heat exchanger formed between the first, second and third control valves of said liquid supplying mechanism and the pump is dipped in the refrigerant in said cooling tank.

* * * * *